United States Patent
Clacens et al.

(10) Patent No.: US 9,522,898 B2
(45) Date of Patent: Dec. 20, 2016

(54) OXIDATION OF ALCOHOL COMPOUNDS VIA MESOSTRUCTURED VPO CATALYSTS

(71) Applicants: RHODIA OPERATIONS, Paris (FR); Centre National De La Recherche Scientifique, Paris (FR)

(72) Inventors: Jean-Marc Clacens, Saint-Julien-l'Ars (FR); Floryan Decampo, Pittsburgh, PA (US); Fabien Grasset, Grasse (FR); Benjamin Katryniok, Loos-en-Gohelle (FR); Franck Dumeignil, Fretin (FR); Sebastien Paul, Thun-Saint-Amand (FR); Veronique Rataj, Pont-a-Marcq (FR)

(73) Assignees: RHODIA OPERATIONS, Paris (FR); CENTRE NATIONAL DE LA RECHERECHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/765,855

(22) PCT Filed: Feb. 5, 2014

(86) PCT No.: PCT/EP2014/052188
§ 371 (c)(1),
(2) Date: Aug. 5, 2015

(87) PCT Pub. No.: WO2014/122142
PCT Pub. Date: Aug. 14, 2014

(65) Prior Publication Data
US 2015/0368218 A1    Dec. 24, 2015

(30) Foreign Application Priority Data

Feb. 8, 2013    (WO) ................ PCT/CN2013/071563

(51) Int. Cl.
| | | |
|---|---|---|
| C07D 307/46 | (2006.01) |
| C07C 45/38 | (2006.01) |
| B01J 21/18 | (2006.01) |
| B01J 27/198 | (2006.01) |

(52) U.S. Cl.
CPC .............. *C07D 307/46* (2013.01); *B01J 21/18* (2013.01); *B01J 27/198* (2013.01); *C07C 45/38* (2013.01)

(58) Field of Classification Search
None
See application file for complete search history.

(56) References Cited

U.S. PATENT DOCUMENTS

2003/0130528 A1* 7/2003 Grushin ............... C07D 307/46
549/483

OTHER PUBLICATIONS

Carreon, Moises. Studies in Surface Science and Catalysis 141 (2002) 301-308.*
Merck Index (12th ed., Merck: Whitehouse Station, NJ, 1996; entry 1159 on p. 189 for "benzyl alcohol" and entry 4325 on p. 729 for "furfuryl alcohol").
Bordes, E. "Crystallochemistry of V-P-O Phases and Application to Catalysis" Catal. Today (1987), 1, pp. 499-526.
Carreon et al. "Ordered mesostructured mixed metal oxides: microporous VPO phases for n-butane oxidation to maleic anhydride" Catalysis Letters (2004) vol. 92, pp. 11-16.

* cited by examiner

*Primary Examiner* — Golam M M Shameem
*Assistant Examiner* — Laura Daniel

(57) ABSTRACT

The present invention concerns a process for the production of an aldehyde compound by an oxidation reaction of an alcohol compound in the presence of a mesostructured vanadium phosphorus mixed oxide catalyst, at a temperature comprised between 50° C. and 200° C., in presence of an oxidant. The reaction medium may also comprise a solvent.

13 Claims, No Drawings

OXIDATION OF ALCOHOL COMPOUNDS VIA MESOSTRUCTURED VPO CATALYSTS

CROSS-REFERENCE TO RELATED APPLICATIONS

This application is a U.S. national phase entry under 35 U.S.C. §371 of International Application No. PCT/EP2014/052188, filed on Feb. 5, 2014, which claims priority to International Application No. PCT/CN2013/071563, filed on Feb. 8, 2013, the entirety of which is being incorporated herein by reference for all purposes.

The present invention concerns a process for the production of an aldehyde compound by an oxidation reaction of an alcohol compound in the presence of a mesostructured vanadium phosphorus mixed oxide catalyst, at a temperature comprised between 50° C. and 200° C., in presence of an oxidant. The reaction medium may also comprise a solvent.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

HMF (hydroxymethyl furfural) is considered as a key platform molecule in the transformation of biomass into chemicals. However, HMF that can be derived from sugars, such as fructose or glucose, is not stable and is difficult to isolate easily. On the contrary, DFF (2,5-diformylfuran), which can be obtained by selective oxidation of HMF is more stable and could be easily isolated for direct use or as an intermediate for other molecules or polymers.

Selective oxidation of 5-hydroxymethyl furfural into 2,5-diformylfuran has been described using homogeneous catalysts such as Co/Mn/Br/Zr acetates mixture (Partenheimer W., Gruchin V. V., *Adv. Synth. Catal.* (2001) 343 (1):102-111) or homogeneous vanadium complexes (Hanson S. K., Wu R., Silks L. A. P. *Org. Lett.* (2011) 13(8):1908-1911. However, the use of heterogeneous catalysts with $O_2$ is preferred due to its easy separation from the reaction products.

Vanadium oxides $V_2O_5$ have then been used in WO9617836A2 publication with a weight ratio of 2 between the catalyst and the 5-HMF. After 1 h 30 of reaction at 170° C. under air at 10 bar in toluene, the conversion is 91% and the yield 62%. By supporting $V_2O_5$ on $TiO_2$, keeping the ratio between the catalyst and the 5-HMF at 2, they manage to obtain a quantitative conversion with a yield of 97% in 1 h 30 at 110° C. under air at 16 bar in toluene. However, this type of supported vanadium oxides have been recently studied by Nie and the selectivity toward DFF reported were always below 70% (Nie J., Liu H. *Pure Appl. Chem.* (2012) 84(3):765-777).

Flow chemical oxidation was performed using supported 5% w/w $Pt/SiO_2$ but only yielded to 60% 5-HMF conversion and 70% selectivity toward DFF at 100° C. under 150 psi of air (Lilga M. A., Hallen R. T., Gray M. *Top. Catal.* (2010) 53: 1264-1269).

The best selectivity was reported with the use of ICaT-4 15% w/w silver substituted calcined manganese mesoporous material (catalyst/5-HMF weigh ratio of 1) under 15 bar of air at 165° C. in isopropanol which gave 100% selectivity toward DFF with an HMF conversion of 98% in 4 h. This very high temperature is required to get a full conversion, with a 60% conversion at 135° C.

Several studies have reported catalytic systems capable of selectively oxidizing HMF into DFF and in particular the family of vanadium phosphates.

Vanadium oxides and Vanadium phosphates oxides were reported by WO03024947A2 publication for the oxidation of the 5-HMF directly formed by dehydration of fructose without any purifications. $V_2O_5$ used in DMSO at 150° C. under air bubbling leads to 58% yield of DFF after 13 h based on the HMF formed. They screened other vanadium oxides such as $VOPO_4$ or $VOHPO_4.0.5H_2O$ on the oxidation of commercial 5-HMF in DMSO with air bubbling for 5 h and a weight ratio of 0.5 between the catalyst and the 5-HMF at 150° C. The best results showed complete conversion with more than 80% yield in DFF. The use of DMSO makes the recovery of DFF difficult.

Carlini tried then to use $VOPO_4.2H_2O$ in a 0.4 weight ratio with 5-HMF under 1 bar of $O_2$ in MIBK at 80° C. After 6 h and 98% conversion of 5-HMF, the selectivity toward DFF was 50% (Carlini C., Patron P., Raspolli Galleti A. M., Sbrana G., Zima V. *Appl. Catal. A: Gen.* (2005) 289:197-204). The use of the toxic high boiling point solvent dimethyl formamide at 100° C. increased the selectivity at 93% with a decrease in conversion at 56%. The incorporation of iron in the structure of the vanadium catalyst made it possible to decrease the ratio between the catalyst and the 5-HMF to 0.01 keeping a high selectivity at 87% and moderate conversion at 59%.

However, these studies on the family of vanadium phosphates mixed oxides indicate that it is very difficult to obtain high conversions and selectivity into DFF and typically high loading of catalysts or high temperatures are required. The vanadium phosphate mixed oxide catalysts have been then demonstrated to be active in the reaction transforming HMF into DFF with limited conversion and selectivity. In the objective of developing an industrialisable process there is a need to uncover new catalysts that can be more active and selective.

SUMMARY OF THE INVENTION

It appears now that the current invention shows that the activity and selectivity of the this family of catalysts can be tuned and optimized by using surfactant additives within the structure of the catalysts to produce a mesostructured vanadium phosphorus mixed oxide catalyst. Such a modification allows to significantly improve the activity of the catalysts as well as their selectivity in the same conditions.

The present invention concerns then a process for the production of an aldehyde compound by an oxidation reaction of at least an alcohol compound in the presence of at least a mesostructured vanadium phosphorus mixed oxide catalyst, at a temperature comprised between 50° C. and 200° C., in presence of an oxidant.

The invention also concerns a process for the production of an aldehyde compound, comprising at least the following steps:

(a) preparation of a mesostructured vanadium phosphorus mixed oxide catalyst by mixing a phosphorus mixed oxide compound with a surfactant in an aqueous solution and heating to produce a mesostructured vanadium phosphorus mixed oxide catalyst; and (b) oxidation reaction of at least an alcohol compound in the presence of at least a mesostructured vanadium phosphorus mixed oxide catalyst, at a temperature comprised between 50° C. and 200° C., in presence of an oxidant.

The invention also concerns a product susceptible to be obtained by said process.

The present invention provides then a process permitting to reach a high yield and conversion of the alcohol compound to the corresponding aldehyde compound, by the use of a very active family of mesostructured vanadium phosphorus mixed oxide catalyst.

DETAILED DESCRIPTION

Throughout the description, including the claims, the term "comprising one" should be understood as being synonymous with the term "comprising at least one", unless otherwise specified, and "between" should be understood as being inclusive of the limits.

"Alkyl" as used herein means a straight chain or branched saturated aliphatic hydrocarbon. Preferably alkyl group comprises 1-20 carbon atoms. Representative saturated straight chain alkyls include methyl, ethyl, n-propyl, n-butyl, n-pentyl, and the like; while saturated branched alkyls include isopropyl, sec-butyl, isobutyl, tert-butyl, isopentyl, and the like.

"Alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbon atoms of the alkenyl group. Representative unsaturated straight chain alkenyls include ethenyl, propenyl, butenyl, pentenyl, hexenyl, heptenyl, octenyl, nonenyl, decenyl and the like.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups.

"Aryl" as used herein means a 6-carbons monocyclic or 10-carbons bicyclic aromatic ring system wherein 0, 1, 2, 3, or 4 atoms of each ring are substituted. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Cycloalkyl" as used herein means cycloalkyl groups containing from 3 to 8 carbon atoms, such as for example cyclohexyl.

"Heterocyclic" as used herein means heterocyclic groups containing up to 6 carbon atoms together with 1 or 2 heteroatoms which are usually selected from O, N and S, such as for example radicals of: oxirane, oxirene, oxetane, oxete, oxetium, oxalane (tetrahydrofurane), oxole, furane, oxane, pyrane, dioxine, pyranium, oxepane, oxepine, oxocane, oxocinc groups, aziridine, azirine, azirene, azetidine, azetine, azete, azolidine, azoline, azole, azinane, tetrahydropyridine, tetrahydrotetrazine, dihydroazine, azine, azepane, azepine, azocane, dihydroazocine, azocinic groups and thiirane, thiirene, thiethane, thiirene, thietane, thiete, thietium, thiolane, thiole, thiophene, thiane, thiopyrane, thiine, thiinium, thiepane, thiepine, thiocane, thiocinic groups.

"Heterocyclic" may also mean a heterocyclic group fused with a benzene-ring wherein the fused rings contain carbon atoms together with 1 or 2 heteroatom's which are selected from N, O and S.

Mesostructured vanadium phosphorus mixed oxide catalyst of the present invention maybe be a material exhibiting a XRD diffraction angle theta comprised between 1° and 5°, notably comprised between and 0.5° and 2.5°. A mesostructured material is generally considered as an ordered material having a structure that may be lamellar, cubic, hexagonal and/or porous with dimensions intermediate between micro and macro levels. Angle theta measured by XRD diffraction may notably be obtained by a method involving a powdered X-ray diffraction on the basis of the Bragg law.

The BET specific surface area of the mesostructured vanadium phosphorus mixed oxide catalyst may be of at least 10 $m^2/g$, preferably between 10 $m^2/g$ and 100 $m^2/g$, more preferably between 10 $m^2/g$ and 50 $m^2/g$. In the continuation of the description, the term "specific surface" is understood to mean the BET specific surface determined by nitrogen adsorption in accordance with standard ASTM D 3663-78 laid down from the Brunauer-Emmett-Teller method described in the periodical "The Journal of the American Chemical Society, 60, 309 (1938)".

Meso structured vanadium phosphorus mixed oxide catalysts may be prepared by addition of a phosphorus mixed oxide compounds with a surfactant in an aqueous solution and heating to produce said mesostructured vanadium phosphorus mixed oxide catalysts. Meso structured lamellar, hexagonal and cubic vanadium-phosphorus-oxides are indeed known to be prepared by employing cationic surfactants, such as alkyl ammonium bromides, anionic surfactants, such as sulfonates and phosphonates, and alkylamine surfactants. In a typical synthesis, an aqueous solution containing the phosphorus and vanadium sources was added to an aqueous surfactant solution (M. A Carreon, V. V. Guliants, *Studies in Surface Science and Catalysis* 141 (2002) 301/M. A. Carreon, V. V. Guliants, *Microporous and Mesoporous Materials* 5,3, (2002) 297).

Without being bound to any particular theory, there have been a number of models proposed to explain the formation of mesoporous materials and to provide a rational basis for the various synthesis routes. On the most common level, these models are predicated upon the presence of surfactants in a solution to guide the formation of the inorganic mesostructure from the solubilized inorganic precursors group and a long hydrophobic tail group within the same molecule and will self-organize in such a way as to minimize contact between the incompatible ends. How the inorganic precursor interacts with the surfactant is the issue whereby the models diverge; the type of interaction between the surfactant and the inorganic precursor will be seen as a significant difference among the various synthesis routes, the formation models, and the resulting classes of mesoporous materials.

Meso structured vanadium phosphorus mixed oxide catalysts are preferably prepared from the following compounds: $VO(PO_3)_2$, $(VO)_2P_2O_7$, $VOPO_4$, $VOPO_4\text{-}2H_2O$, and $VOHPO_4\text{-}0.5H_2O$.

Surfactants that can be used in the present invention may notably be non ionic surfactants or ionic surfactants such as cationic surfactants.

Preferably surfactants may be tetralkyl ammonium salts such as halogen salts, for example tetralkyl ammonium bromide or be tetralkyl ammonium chloride. Alkyls of the tetralkyl ammonium salts may be a hydrocarbon chain comprising from 1 to 20 carbon atoms notably comprising one or several functions such as —OH and/or —$NH_2$.

More preferably surfactants of the present invention may be alkyl trimethyl ammonium salts, such as halogen salts. Alkyl of the alkyl trimethyl ammonium salts may be a hydrocarbon chain comprising from 4 to 20 carbon atoms notably comprising one or several functions such as —OH and/or —NH$_2$. Alkyl can notably be C$_{10}$, C$_{12}$, C$_{14}$, C$_{16}$ and C$_{18}$.

Surfactants may also be alkyl-amines wherein the alkyl chain comprises from 1 to 20 carbon atoms notably comprising one or several functions such as —OH and/or —NH$_2$.

Surfactants of the present invention are particularly chosen in the group consisting of: C$_{12}$H$_{25}$NMe$_3$Br, C$_{14}$H$_{29}$NMe$_3$Br, and C$_{16}$H$_{33}$NMe$_3$Br, and C$_{12}$H$_{25}$NH$_2$.

Temperature of the reaction to produce the mesostructured vanadium phosphorus mixed oxide catalysts may be comprised between 50° C. and 120° C., preferably between 60° C. and 100° C. pH of the reaction medium may be comprised between 0 and 10, notably between 0 and 7.5, preferably between 1 and 3. pH may notably be adjusted at the start of the reaction accordingly.

The resulting compound may be recovered by vacuum filtration, washed with water and notably dried. It is also possible to proceed to a post-treatment such as a hydrothermal treatment at a temperature comprised between 100° C. and 180° C., and/or a calcination treatment at a temperature comprised between 200° C. and 500° C., under air or nitrogen.

The alcohol compound of the present invention may comprise at least a primary alcohol. It's perfectly possible according to one embodiment of the present invention that the above defined alcohol may also be used as a solvent in the reaction medium.

The alcohol compound may notably be a compound of formula (I)

R—(OH)$_x$     (I)

Wherein:
x is 1, 2 or 3, and
R is a straight, branched or cyclic hydrocarbon group.

R may represent straight, branched or cyclic hydrocarbon group, preferably comprising from 1 to 30 carbon atoms, that can be an alkyl, alkenyl, aryl, cycloalkyl or heterocyclic group, notably comprising one or several heteroatoms such as O, S, F, and N. Preferred groups for R may be for example: alkyl, cyclic alkane, cyclic alkene, phenyl, furanyl, and tetrahydrofuranyl.

In addition the alcohol compound may comprise additional functionalities, such as an aldehyde function, carboxylic acid function, and amine function.

Preferred alcohol compounds of the present invention, such as compounds of formula (I), are chosen in the group consisting of: furfuryl alcohol, 2,5 furandimethanol, 2,5-tetrahydrofuranedimethanol, benzyl alcohol, 1,6-hexandiol, 1,3 butanediol, 1,7-heptanediol, 5-hydroxymethyl furan-2-carboxaldehyde (5-HMF), and 1,4-Benzenedimethanol.

The aldehyde compound produced with the process of the present invention may be chosen in the group consisting of: furfural, 2,5 furandicarboxaldehyde (DFF), 2,5-tetrahydro-furanedicarboxaldehyde, benzaldehyde, 1,6-hexanedial (adipaldehyde), 3-oxobutanal, 1,7-heptanedial, and 1,4-benzenedicarboxaldehyde (terephtaldehyde).

When the reaction medium comprises a solvent, the amount of the alcohol compound in the reaction medium, notably at the start of the reaction, may be comprised between 0.01 and 1 mol/L, preferably between 0.05 and 0.2 mol/L.

Weight amount of the mesostructured vanadium phosphorus mixed oxide catalyst in the reaction medium, notably at the start of the reaction, may be comprised between 1 and 80 wt %, preferably between 40 and 80 wt %, based on the weight of the alcohol compound.

The reaction medium may comprise at least one solvent. By "solvent" is meant a single solvent or a combination of suitable solvents. Solvent used in the reaction medium of the present process may be organic or inorganic.

Solvent is preferably a non polar solvent, such as:
alkane solvent, as pentane, hexane,
alkyl cyclic solvent, as cyclopentane, cyclohexane,
aromatic solvent, such as benzene, toluene, m-xylene, p-xylene
chlorine solvent such as chloroform
ether solvent such as 1,4-dioxolane The oxidant in the processes of the present invention is preferably an oxygen-containing gas or gas mixture, such as, but not limited to air. Oxygen by itself is also a preferred oxidant. Other oxidants that are suitable include hydrogen peroxide or organic hydroperoxide.

The preferred temperature range will vary with catalyst used but is about 70° C. to 150° C., preferably about 80° C. to 120° C. As described above, the reaction will occur faster at higher temperatures. Because the HMF to DFF reaction is a heterogeneous reaction catalyzed by vanadium compounds, the time needed to reach approximately 100% conversion will depend, among other factors, on (i) reaction temperature, (ii) stirring efficiency, (iii) air/oxygen flow through the liquid phase, (iv) type of catalyst used, (v) catalyst amount, (vi) the amount of water produced in the first step (as large quantities of water decrease catalytic activity), (vii) catalyst dispersion, (viii) presence or absence of catalytic poisons resulting from side-products formed in the first step. The time of reaction also will vary with reaction conditions and desired yield, but is generally about 1 to about 24 hours, preferably about 1 to about 10 hours. The reaction may be conducted under pressure of air or oxygen. Agitation may also be used.

The aldehyde compound formed above may optionally be isolated from the reaction mixture using any known means, such as but not limited to liquid-liquid extraction, crystallization, vacuum distillation/sublimation, and dilution with water and extraction with a suitable organic solvent, such as dichloromethane. If an aromatic solvent is used as the solvent in the reaction mixture, a preferred method is liquid-liquid purification with a solvent such as water.

The present invention will be detailed below with reference to the following Examples, but not limited by them.

EXAMPLES

Example 1

Preparation of Mesostructured C$_{14}$ VOPO$_4$ and C$_{14}$ VOHPO$_4$

To an aqueous solution (120 mL) of tetradecyl trimethyl-ammonium bromide (3.4 g, 0.01 mol) was added VOPO$_4$.2H$_2$O (2.0 g, 0.01 mol). The pH was adjusted to approximately 7.5 with aqueous concentrated NH$_3$ and heated at 74° C. for 48 h. The brown solid was recovered by vacuum filtration, washed with water (4×250 mL) and dried 3 days in an oven at 50° C. The same procedure was applied starting from VOHPO$_4$.0.5H$_2$O leading to C$_{14}$ VOHPO$_4$.

Results concerning XRD theta angle and BET surface area of the obtained products are mentioned in Table 1.

TABLE 1

| Test | Catalyst | XRD theta angle (°) | BET surface area ($m^2/g$) |
|---|---|---|---|
| C1 | $VOPO_4$ $2H_2O$ | 5.95 | <1 |
| C2 | $VOPO_4$ $2H_2O$ | 5.95 | <1 |
| C3 | $VOHPO_4$ $0.5H_2O$ | 7.74 | 9.4 |
| C4 | $VOPO_4$ $2H_2O$ | 5.95 | <1 |
| C5 | $VOHPO_4$ $0.5H_2O$ | 7.74 | 9.4 |
| 1 | $C_{14}$ $VOHPO_4$ | 1.50 | 26.7 |
| 2 | $C_{14}$ $VOPO_4$ | 1.31 | 18.4 |
| 3 | $C_{14}$ $VOPO_4$ | 1.31 | 18.4 |
| 4 | $C_{14}$ $VOPO_4$ | 1.31 | 18.4 |
| 5 | $C_{14}$ $VOPO_4$ | 1.31 | 18.4 |

XRD theta angles were determined on grounded samples desposited on glass powder XRD sample holders. Data was collected in a theta range of 0.5 to 100° (0.0°/sec and 1 s/step) using a device in Bragg-Brentano configuration at room temperature.

BET surface areas were determined on grounded samples. Samples were degazed at 80° C. for at least 3 h prior to analysis by nitrogen adsorption in accordance with standard ASTM D 3663-78.

Example 2

Catalytic Oxidation of 5-HMF

5-HMF is reacted in presence of several catalysts to produce DFF, in presence of organic solvents for 6 hours with 1 atm $O_2$. Results are mentioned in Table 2.

TABLE 2

| Test | Catalyst | [5-HMF] (mol/L) | Cat/HMF (wt %) | Solvent (mL) | T (° C.) | Conversion (%) | Yield DFF (%) |
|---|---|---|---|---|---|---|---|
| C1 | $VOPO_4$ $2H_2O$ | 0.3 | 20 | Toluene (40) | 80 | 18 | 5 |
| C2 | $VOPO_4$ $2H_2O$ | 0.2 | 40 | DMF (50) | 100 | 53 | 41 |
| C3 | $VOHPO_4$ $0.5H_2O$ | 0.16 | 48 | DMSO (5) | 150 | 88 | 69 |
| C4 | $VOPO_4$ $2H_2O$ | 0.1 | 29 | Toluene (3) | 110 | 85 | 4 |
| C5 | $VOHPO_4$ $0.5H_2O$ | 0.1 | 29 | Toluene (3) | 110 | 80 | 6 |
| 1 | $C_{14}$ $VOHPO_4$ | 0.1 | 81 | Toluene (3) | 110 | 99 | 82 |
| 2 | $C_{14}$ $VOPO_4$ | 0.1 | 81 | Toluene (3) | 110 | 99 | 82 |
| 3 | $C_{14}$ $VOPO_4$ | 0.1 | 40 | Toluene (3) | 110 | 99 | 73 |
| 4 | $C_{14}$ $VOPO_4$ | 0.1 | 40 | m-xylene (3) | 110 | 99 | 67 |
| 5 | $C^{14}$ $VOPO_4$ | 0.1 | 40 | p-xylene (3) | 110 | 99 | 63 |

Tests C1 and C2 of the Table 1 were taken from Carlini C., Patron P., Raspolli Galleti A. M., Sbrana G., Zima V. *Appl. Catal. A: Gen.* (2005) 289:197-204. Test C3 was taken from WO 03024947. Tests C4 and C5 stand as reference in order to attest the influence of the introduction of ammonium in the vanadium catalyst. A lack of selectivity toward is observed both with $VOPO_4.2H_2O$ and $VOHPO_4.0.5H_2O$ with yields below 6%.

Tests 1-3 reveal the strong positive impact of the introduction of ammoniums in the vanadium catalyst on the yield and the selectivity toward DFF, both on $C_{14}/VOPO_4$ and $C_{14}/VOHPO_4$ catalysts.

Example 3

Preparation of Several Mesostructured $VOPO_4$

Mesostructured $VOPO_4$ are produced according the method of example 1 except the use of several surfactant compounds such as $C_{12}H_{25}NMe_3Br$, $C_{14}H_{29}NMe_3Br$, and $C_{16}H_{33}NMe_3Br$, and $C_{12}H_{25}NH_2$ Example 4

Catalytic Oxidation of 5-HMF

5-HMF is reacted in presence of several catalysts to produce DFF, in presence of organic solvents for 6 hours with 1 atm $O_2$. Results are mentioned in Table 3.

TABLE 3

| Test | Catalyst | [5-HMF] (mol/L) | Cat/HMF (wt %) | Solvent (mL) | T (° C.) | Conversion (%) | Yield DFF (%) |
|---|---|---|---|---|---|---|---|
| 1 | $C_{12}$ $VOPO_4$ | 0.1 | 40 | Toluene (3) | 110 | 90 | 74 |
| 2 | $C_{14}$ $VOPO_4$ | 0.1 | 40 | Toluene (3) | 110 | 91 | 83 |
| 3 | $(C_{14})_2$ $VOPO_4$ | 0.1 | 40 | Toluene (3) | 110 | 87 | 76 |
| 4 | $C_{16}$ $VOPO_4$ | 0.1 | 40 | Toluene (3) | 110 | 76 | 84 |
| 5 | $C_{12}NH_2$ $VOPO_4$ | 0.1 | 80 | Toluene (3) | 110 | 99 | 83 |

It appears then that good yield and conversion are obtained with the process of the present invention with several variations regarding to the surfactant compounds used to produce the mesostructured VPO catalysts.

The invention claimed is:

1. A process for the production of an aldehyde compound, the process comprising oxidizing an alcohol compound in the presence of a mesostructured vanadium phosphorus mixed oxide catalyst, at a temperature comprised between 50° C. and 200° C., in the presence of an oxidant; wherein the mesostructured vanadium phosphorus mixed oxide catalyst has been prepared by mixing a vanadium phosphorus mixed oxide compound with a surfactant in an aqueous solution and heating to produce the mesostructured vanadium phosphorus mixed oxide catalyst.

2. The process according to claim 1, wherein the mesostructured vanadium phosphorus mixed oxide catalyst exhibits a XRD diffraction angle theta between 1° and 5°.

3. The process according to claim 1, wherein the mesostructured vanadium phosphorus mixed oxide catalyst provides a BET specific surface area of at least 10 $m^2/g$.

4. The process according to claim 1, wherein the mesostructured vanadium phosphorus mixed oxide catalysts is prepared from a compound selected from the group consisting of: $VO(PO_3)_2$, $(VO)_2P_2O_7$, $VOPO_4$, $VOPO_4$-$2H_2O$, and $VOHPO_4$-$0.5H_2O$.

5. The process according to claim 1, wherein the surfactant is a non ionic surfactant or an ionic surfactant.

6. The process according to claim 1, wherein the surfactant is a tetralkyl ammonium salt.

7. The process according to claim 1, wherein the surfactant is selected from the group consisting of: $C_{12}H_{25}NMe_3Br$, $C_{14}H_{29}NMe_3Br$, and $C_{16}H_{33}NMe_3Br$, and $C_{12}H_{25}NH_2$.

8. The process according to claim 1, wherein the alcohol compound is a compound of formula (I)

R—(OH)$_x$    (I)

wherein:
   x is 1, 2 or 3, and
   R is a straight, branched or cyclic hydrocarbon group.

9. The process according to claim 1, wherein the alcohol compound is selected from the group consisting of: furfuryl alcohol, 2,5 furandimethanol, 2,5-tetrahydrofuranedimethanol, benzyl alcohol, 1,6-hexandiol, 1,3 butanediol, 1,7-heptandiol, 5-hydroxymethyl furan-2-carboxaldehyde, and 1,4-Benzenedimethanol.

10. The process according to claim 1, wherein the aldehyde compound is selected from the group consisting of: furfural, 2,5 furandicarboxaldehyde, 2,5-tetrahydrofuranedicarboxaldehyde, benzaldehyde, 1,6-hexanedial, 3-oxobutanal, 1,7-heptanedial, and 1,4-benzenedicarboxaldehyde.

11. The process according to claim 1, wherein the weight amount of the mesostructured vanadium phosphorus mixed oxide catalyst in the reaction medium is between 1 and 80 wt %, based on the weight of the alcohol compound.

12. The process according to claim 1, wherein the reaction medium comprises at least one solvent.

13. The process according to claim 12, wherein the solvent is a non polar solvent selected from the group consisting of: alkane solvent, alkyl cyclic solvent, aromatic solvent, chlorine solvent and ether solvent.

* * * * *